United States Patent
Andersson

(10) Patent No.: US 11,454,345 B2
(45) Date of Patent: Sep. 27, 2022

(54) REDUCTION OF MICROBIOLOGICAL GROWTH IN PIPES

(71) Applicant: EPFF ELECTRICAL PIPE FOR FLUID TRANSPORT AB, Kungsor (SE)

(72) Inventor: Thomas Andersson, Kungsor (SE)

(73) Assignee: EPFF ELECTRICAL PIPE FOR FLUID TRANSPORT AB, Kungsor (SE)

( * ) Notice: Subject to any disclaimer, the term of this patent is extended or adjusted under 35 U.S.C. 154(b) by 241 days.

(21) Appl. No.: 16/345,594

(22) PCT Filed: Nov. 1, 2017

(86) PCT No.: PCT/EP2017/077973
§ 371 (c)(1),
(2) Date: Apr. 26, 2019

(87) PCT Pub. No.: WO2018/083127
PCT Pub. Date: May 11, 2018

(65) Prior Publication Data
US 2019/0249815 A1 Aug. 15, 2019

(30) Foreign Application Priority Data
Nov. 1, 2016 (EP) .................................. 16196711

(51) Int. Cl.
*F16L 58/00* (2006.01)
*A61L 2/03* (2006.01)
(Continued)

(52) U.S. Cl.
CPC ............. *F16L 58/00* (2013.01); *A61L 2/03* (2013.01); *F16L 9/125* (2013.01); *F16L 11/127* (2013.01)

(58) Field of Classification Search
CPC .......... F16L 58/00; F16L 9/125; F16L 11/127; A61L 2/03
See application file for complete search history.

(56) References Cited

U.S. PATENT DOCUMENTS 7,094,381 B1 * 8/2006 Overton ................. B03C 1/288
204/660
2008/0053550 A1 3/2008 Hatchett et al.
(Continued)

FOREIGN PATENT DOCUMENTS

AT 506089 6/2009
GB 471318 A 9/1937
(Continued)

OTHER PUBLICATIONS

International Search Report on corresponding PCT application (PCT/EP2017/077973) from International Searching Authority (EPO) dated Feb. 20, 2018.
(Continued)

*Primary Examiner* — Kevin Joyner
(74) *Attorney, Agent, or Firm* — Klein, O'Neill & Singh, LLP

(57) ABSTRACT

The proposed technology relates to a system (8) for preventing microbiological growth in a conduit conveying a liquid. The system (8) comprises a multi-layered pipe (10) constituting said conduit and having an inner layer (12) that covers the complete inside (16) of the pipe (10) and is formed of an electrically conductive polymer material. A liquid in the pipe (10) is in direct contact with the inner layer (12). The system further has a first electrical connector (18) and a second electrical connector (19) connecting to the inner layer (12) from outside the pipe (10), wherein the first electric connector (18) and the second electric connector (19) are spaced apart along the pipe (10). The system further has an electric power source (20) operationally connected to
(Continued)

the first electrical connector (18) and the second electrical connector (19) and configured for supplying an electric current to the inner layer (12).

13 Claims, 4 Drawing Sheets

(51) Int. Cl.
    *F16L 9/12*     (2006.01)
    *F16L 11/127*     (2006.01)

(56) References Cited

U.S. PATENT DOCUMENTS

| | | | | |
|---|---|---|---|---|
| 2011/0259833 | A1* | 10/2011 | Andersson | F16L 58/00 |
| | | | | 210/748.01 |
| 2015/0232352 | A1* | 8/2015 | Chew | B08B 9/027 |
| | | | | 204/554 |
| 2016/0186916 | A1* | 6/2016 | Krishnan | A01G 33/00 |
| | | | | 435/257.1 |

FOREIGN PATENT DOCUMENTS

| | | | | |
|---|---|---|---|---|
| GB | 2442011 | | 3/2008 | |
| GB | 2456367 | A * | 7/2009 | ............ F16L 47/00 |
| JP | H11123384 | A | 5/1999 | |
| JP | H11147598 | A | 6/1999 | |
| JP | 2014511758 | A | 5/2014 | |
| WO | WO 94/07790 | | 4/1994 | |

OTHER PUBLICATIONS

Written Opinion on corresponding PCT application (PCT/EP2017/077973) from International Searching Authority (EPO) dated Feb. 20, 2018.

Office Action from Japanese Patent Office on co-pending JP application (JP 2019-545856) dated Jul. 6, 2021.

\* cited by examiner

REDUCTION OF MICROBIOLOGICAL GROWTH IN PIPES

CROSS-REFERENCE TO RELATED APPLICATION

This application is the National Phase, under 35 U.S.C. § 371(c), of International Application No. PCT/EP2017/077973, filed Nov. 1, 2017, which claims priority from EP 16196711.2, filed Nov. 1, 2016. The disclosures of all of the referenced applications are incorporated herein by reference in their entirety.

FEDERALLY SPONSORED RESEARCH OR DEVELOPMENT

Not Applicable

TECHNICAL FIELD

The proposed technology generally relates to the field of liquid transportation, dispensing, and recycling. In particular, it relates to the reduction of microbiological growth in pipes.

BACKGROUND

Microbiological growth and the formation of biofilms on the inside of pipes is a concern in many applications where a liquid is conveyed. Properties of the liquid as such can be influenced by the microbiological growth and make it less suitable for its intended use. Microbiological growth in a pipe may also increase microbiological growth further downstream in equipment that is routinely cleaned from such growth. Microbiological growth can also detach from inside a pipe and cause clogging or damage in downstream equipment. It is also a known problem that microbiological growth on the inside of a pipe can introduce harmful pathogens in the conveyed liquid.

Three groups of applications where microbiological growth in a pipe can be a problem have been identified, namely liquid transportation, liquid recycling, and liquid dispensing.

An example of liquid transportation is water supply by public utilities. The pipes are used for long periods of time, typically stretching over several decades. Large quantities of microbiological material can build up in the pipes, which reduces the transport capacity of the pipes. The transport may also be over shorter distances, such as in dairy equipment at milk farms.

Examples of applications using liquid recycling where microbiological growth can be a problem are numerous. For example, it may be a problem in centralized domestic cooling of buildings, recycling of washing liquids in car washes, recycling of cutting fluids in metalworking, recycling of liquids in paper mills, and circulating low-temperature heating systems in buildings.

Examples of liquid dispensing applications are also numerous. The microbiological growth may be a problem in beverage dispensing, in particular in dispensing of beer from kegs, in dental equipment, and in domestic water systems, such as showers. The latter is a known source of *legionella*, which may be harmful to people.

There are also more complex systems that fall outside the simple classification above or are combinations of several types of applications, such as dialysis equipment in which liquids are both supplied and recirculated.

Pipes used in the handling of nutritious liquids, such as beer, require frequent cleaning, in particular if the transported liquids are stored at room temperature and cooled first at the dispensing point. This may cause rapid microbiological growth in the pipe conveying the liquids. It is known to cool such pipes to reduce the microbiological growth and prevent deterioration of the conveyed liquids. However, such a technology is typically costly to install and operate.

The cleaning of a pipe is often costly, both in itself and due to interruptions in the operation of the application. It also often requires the pipe to be flushed afterwards, which is not practical in many applications, such as in closed circulation systems and long distance water transportation.

There is a need for pipes in which microbiological growth and the formation of biofilms is reduced. Further, there is a need for pipes that have low installation and operation costs with respect to the prevention of microbiological growth. Replacing pipes in an existing application may be a costly operation. Thus, there is also a need for pipes preventing microbiological growth that can be retrofitted in an existing application.

Throughout these specifications, microbiological growth is understood to encompass the formation of a biofilm. For example, microbiological growth may be colonies of bacteria.

SUMMARY

It is an object of the proposed technology to meet one or more of the abovementioned needs. In a first aspect, this is achieved by a system for preventing microbiological growth and/or the formation of a biofilm in a conduit conveying a liquid. The system comprises a multi-layered pipe constituting said conduit and having an inner layer and an outer layer. The inner layer covers the complete inside of the pipe and is formed of an electrically conductive polymer material, wherein a liquid in the pipe is in direct contact with the inner layer. The outer layer covers at least a portion of the outside of the inner layer and is formed of an electrically insulating polymer material. The system further comprises a first electrical connector connecting to the inner layer from outside the pipe and a second electrical connector connecting to the inner layer from outside the pipe, wherein the first electrical connector and the second electrical connector are spaced apart along the pipe. The system also comprises an electric power source operationally connected to the first electrical connector and the second electrical connector and configured for supplying an electric current to the inner layer, and/or for supplying an electric potential over the first electrical connector and the second electrical connector. The multilayered pipe may be a rigid pipe or a flexible hose.

In a second aspect, a method is provided for retrofitting a system for preventing microbiological growth in an existing conduit for conveying a liquid. The method comprises: providing a system according to the first aspect, and providing the pipe of the system inside the existing conduit.

In a third aspect, the above object is achieved by a method for preventing microbiological growth in the pipe of a system according to the first aspect, wherein the pipe conveys a liquid. The method comprises: supplying an electric current to the inner layer of the pipe with the electric power source.

In a fourth aspect, one or more of the abovementioned needs are met by a system for preventing microbiological growth and/or the formation of a biofilm in a conduit conveying a liquid, wherein the system comprises a singlelayered flexible hose constituting said conduit and having a single layer, wherein the single layer is formed of an electrically conductive polymer material, and wherein a liquid in the hose is in direct contact with the single layer. The system further comprises a first electrical connector connecting to the single layer from outside the hose and a second electrical connector connecting to the single layer from outside the hose, wherein the first electrical connector and the second electrical connector are spaced apart along the hose. Additionally, the system comprises an electric power source operationally connected to the first electrical connector and the second electrical connector and configured for supplying an electric current to the single layer, and/or for supplying an electric potential over the first electrical connector and the second electrical connector.

In a fifth aspect, a method is provided for retrofitting a system for preventing microbiological growth in an existing conduit for conveying a liquid. The method comprises: providing a system according to the fourth aspect, and providing the hose of the system inside the existing conduit.

In a sixth aspect, the above object is achieved by a method for preventing microbiological growth in the hose of a system according to the fourth aspect, wherein the hose conveys a liquid. The method comprises: supplying an electric current to the single layer of the pipe with the electric power source.

The technology of the fourth to sixth aspects is particularly useful in applications where the hose is surrounded by electrically insulating material, for example within an existing plastic pipe.

In a seventh aspect, a beverage dispensing system is provided comprising a tapping station for dispensing the beverage and a beverage conduit for conveying a beverage from a container containing the beverage to the tapping station. The beverage dispensing system further comprises a system for preventing microbiological growth according to the first aspect or the fourth aspect, wherein the pipe or hose forms part of the beverage conduit. The beverage may be beer and the container may be a keg.

Here, and throughout these specifications, that a liquid is in direct contact with the inner layer means that there is no other material between the inner layer and the liquid.

It has been found that when a current is supplied to the inner layer or single layer, microbiological growth and formation of biofilms are significantly reduced. There is no established theory for why this happens, but a proof-of-concept is provided below. Further, the required electric power for operating the proposed systems is low, thus contributing to low operation costs. Further, the fact that the pipes are made of polymer-based materials means that the manufacturing costs are typically low, thus contributing to lower installation costs. A hose allows for a retrofitting inside existing pipes, which also contributes to lower installation costs.

The liquid may comprise water and/or water soluble substances, such as sugars, alcohols and salts. The main component of the liquid may be water.

Detailed Description of the Proposed Technology

Further optional features of the different aspects of the proposed technology are presented below.

The electric current supplied to the inner layer or single layer may be a direct current. The direct current may be below 10 mA, below 1 mA, between 0.1 mA and 1 mA, or between 0.3 mA and 0.7 mA. The electric current may be generated at a voltage between the first electrical connector and the second electrical connector that is below 150 V, below 120 V, between 20 V and 100 V, or between 50 V and 70 V. The power supply may be configured to supply the direct current to the first electrical connector or the second electrical connector at the here listed voltages between the first electrical connector and the second electrical connector. It has been found that the operating parameters described here reduce microbiological growth, in particular in fast flowing sweet water in distribution mains.

The power source may be configured for changing the polarity between the first electrical connector and the second electrical connector. The changing of the polarity may be random in time or follow a predetermined schedule. The polarity may be changed at least once every 12 hours, or at least once every hour. There are indications that the change of polarity will inhibit the microbiological growth.

Alternatively, the electric current supplied to the inner layer or single layer may be an alternating current. The alternating current may be below 10 mA, below 1 mA, between 0.1 mA and 1 mA, or between 0.4 mA and 0.8 mA. The alternating current may be supplied at a voltage between the first electrical connector and the second electrical connector that is below 80 V, below 50 V, between 10 V and 50 V, between 20 V and 50 V, or between 30 V and 50 V. The power supply may be configured to supply the alternating current to the first electrical connector or the second electrical connector at the here listed voltages between the first electrical connector and the second electrical connector. The alternating current may have a frequency between 1 kHz and 5 kHz, or between 1 kHz and 2 kHz. It has been found that the operating parameters described here reduce microbiological growth, in particular in slowly flowing or still sweet water in distribution mains.

The power source may be further configured for supplying the electric current as a pulsed electric current, both for direct current and alternating current. The pulses may have combined pulse length over a period of time that is equal to or less than 50% of the length of the period. It has been found that the microbiological growth is reduced also for pulsed electric currents. The pulsing has the effect of reduced power consumptions, which contributes to lower operation costs. The power source may be further configured for changing the polarity between the first electrical connector and the second electrical connector between pulses. There are indications that this will inhibit the microbiological growth.

Alternatively to the abovementioned voltages at which the direct current and the alternating current are supplied, the electric current may be supplied at a voltage between the first electrical connector and the second electrical connector that is in the range 1 V and 10 V, 2 V and 8 V, or 3 V and 6. It is contemplated that these voltages will have a sufficient effect on the microbiological growth.

Alternatively, the electric current supplied to the inner layer or single layer may be a direct current or an alternating current below 10 mA, below 1 mA, between 0.1 mA and 1 mA, or between 0.4 mA and 0.8 mA. Additionally, the electric current may be supplied at a voltage between the first electrical connector and the second electrical connector that is in the range 0.5 kV and 6 kV, 0.5 kV and 4 kV, 0.5 kV and 2 kV, or 0.5 kV and 1 kV. Additionally or alternatively, the electric current may be pulsed. Further, the pulses of the electric current may have a pulse length in the range 1 ms and 500 ms, 1 ms and 100 ms, or 1 ms and 10 ms. It is contemplated that these operation parameter will have a significant effect on the microbiological growth.

The power source may be configured for varying the electric current and/or the electric potential randomly or according to predetermined values. The varying of the electric current and/or the electric potential may correspond to relative changes in the range 0.01 to 100, or 0.1 to 10. Additionally, the power source may be configured for varying the electric current and/or the electric potential randomly in time or according to predetermined schedule. The varying may result in a change of the electric current and/or the electric potential at least once every 12 hours, or at least once every hour. It is contemplated that the varying of these parameter will disturb the microbiological growth.

The system may be configured for generating an electric current in the inner layer and an electric current in the liquid, and the electric current in the inner layer may be of the same order of magnitude as the electric current in the liquid, or the electric current in the inner layer may be in the range 0.02 to 50, or 0.1 to 10, times the electric current in the liquid. Additionally or alternatively, the system may be configured for generating an electric current between the inner layer and the liquid corresponding to an electric power in the range 0.01 mW to 500 mW, 0.1 mW to 100 mW, 0.5 mW to 50 mW, or 1 mW to 10 mW per unit area of the inside of the pipe. It should be noted that the parameter determined here depends on the properties of the inner layer and the liquid and can be determined by modeling or experiment.

The electrically conductive polymer material of the inner layer or the single layer may be a carbon-black filled polymer. Additionally or alternatively to carbon-black, the polymer may be filled with nanotubes, graphene, and/or metal fibers or filaments for providing the electrical conductivity. These materials typically have the advantage that a smaller amount of the material is required than for carbon-black for achieving a desired electrical conductivity.

In the case of a pipe, the electrically conductive polymer material may comprise or be composed of polyethylene, polypropylene, polyamide, or polyester. The polymer material of the electrically insulating polymer material, i.e. the outer layer, may comprise or be composed of polyethylene, polypropylene, polyamide, or polyester. In the case of a hose, the electrically conductive polymer material may comprise or be composed of polyethylene, polypropylene, polyamide, or polyester. The polymer material of the electrically insulating polymer material, i.e. the outer layer may comprise or be composed of polyethylene, polypropylene, polyamide, or polyesters.

Carbon black as such may contribute to an increased microbiological growth on the inside of the pipe or hose in the absence of an electric current. However, together with the electric current in the inner layer or single layer, it has been shown that the net effect will be a reduced microbiological growth.

The resistance between the first electrical connector and the second electrical connector of the of the inner layer multiplied with the inside diameter of the pipe and divided by the length between the first electrical connector and the second electrical connector may be in the range 0.2 kΩ to 10 kΩ, 0.5 kΩ to 7 kΩ, or 1 kΩ to 5 kΩ. Here, the resistance is determined without a liquid in the pipe. It has been found that pipes with these parameters are suitable for clean to moderately dirty water.

The first electrical connector and the second electrical connector may be spaced apart by a separation in the range 0.2 m to 50 m, or 1 m to 10 m.

BRIEF DESCRIPTION OF THE DRAWINGS

A more complete understanding of the proposed technology and other features and advantages of the proposed technology, will be apparent from the following detailed description of the figures, where.

DETAILED DESCRIPTION OF EMBODIMENTS OF THE PROPOSED TECHNOLOGY

Figure 1A:
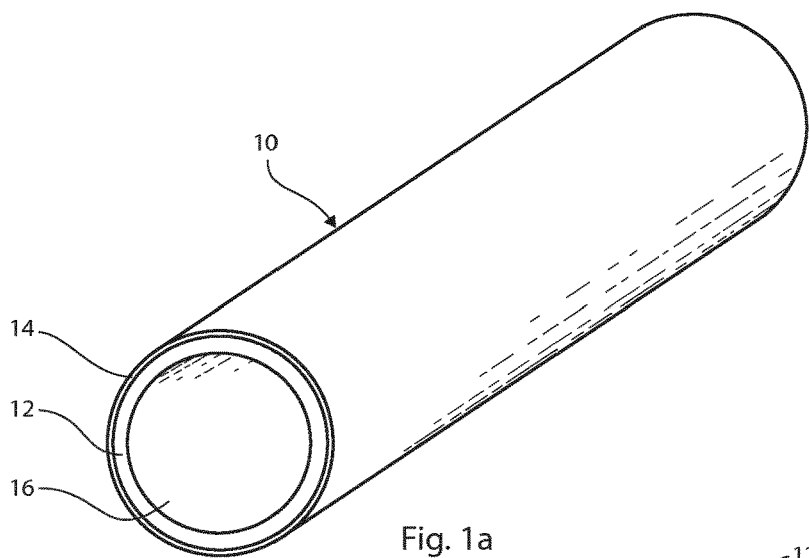
FIGS. 1a-c schematically illustrate the a setup of an embodiment of the proposed system, FIG. 2 schematically illustrates an embodiment of the proposed system in a liquid transportation application, FIG. 3 schematically illustrates an embodiment of the proposed system in a liquid dispensing application, FIG. 4 schematically illustrates an embodiment of the proposed system in a liquid recycling application, FIG. 5 schematically illustrates an embodiment of a beverage dispensing system including the proposed system for preventing microbiological growth, FIG. 6 schematically illustrates an embodiment of a beverage dispensing system including a retrofitted proposed system for preventing microbiological growth.
Figure 1B:
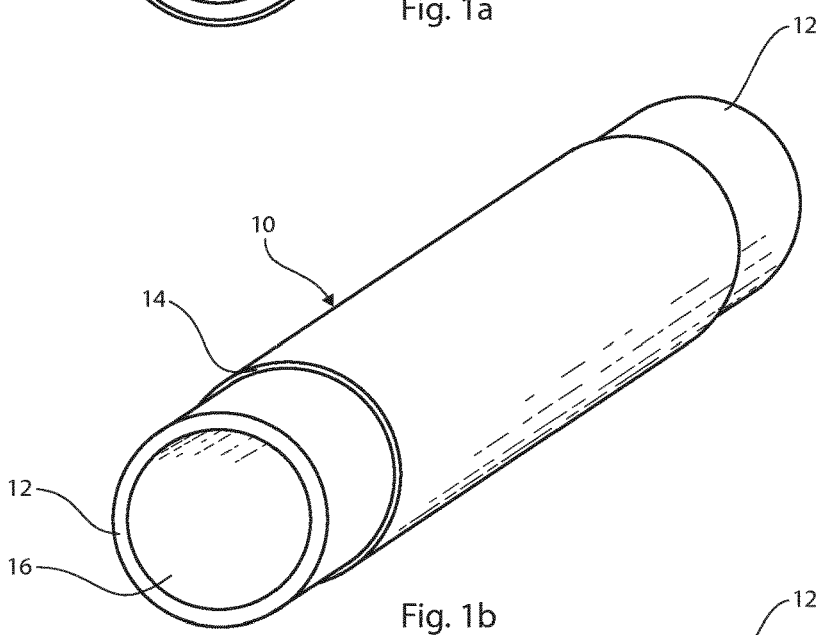
Figure 1C:
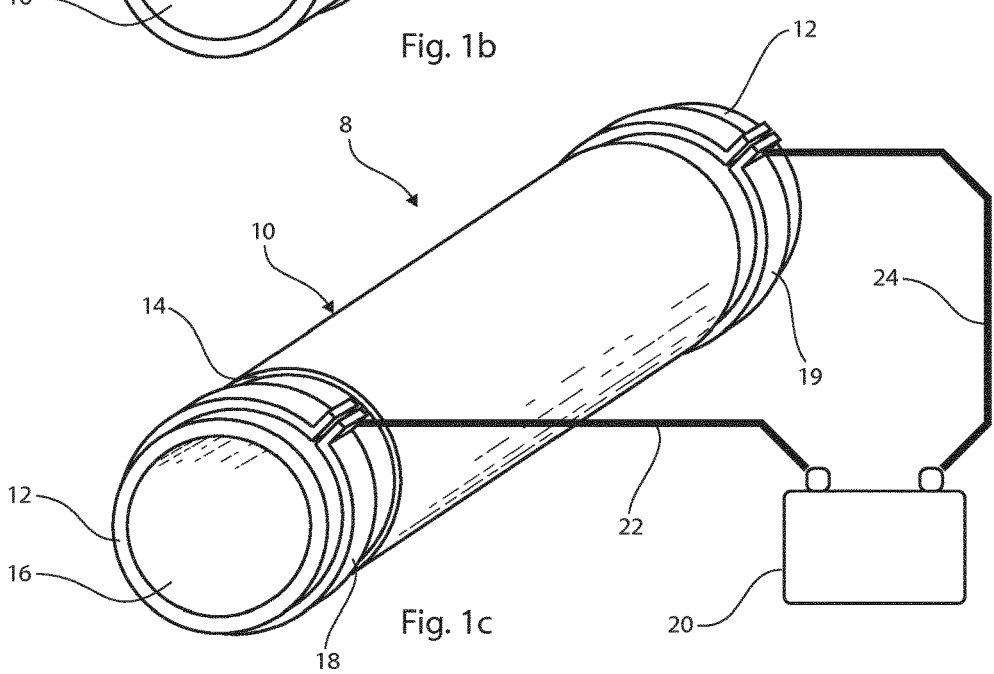

The setup of an embodiment of a system for reducing microbiological growth in a conduit is schematically illustrated in FIGS. 1a-c. A multi-layered pipe 10 is provided having an inner layer 12 and an outer layer 14. The inner layer 12 is composed of carbon-black filled polyethylene with a 20 weight percentage of carbon-black. The outer layer is composed of polyethylene. This means that the inner layer 12 is electrically conductive and the outer layer 14 is electrically insulating. The inner layer 12 and the outer layer 14 have been co-extruded in a manner such that the inner layer 12 covers the complete inside 16 of the pipe 10 and the outer layer 14 covers the complete outside of the inner pipe 12, as is shown in FIG. 1c. There is no material between the inner pipe 12 and a liquid conveyed by the pipe 10.

In an alternative embodiment, the polymer of the inner layer 12 and the outer layer 14 is polyethylene, which means that the pipe 10 will have the properties of a hose with respect to manual handling.

The outer layer 14 is removed at the ends of the pipe 10, thereby making the inner layer 12 accessible from outside the pipe 10, as is shown in FIG. 1b. In alternative embodiments, the outer layer 14 is removed at other parts of the pipe 10, for example further in from the ends of the pipes, thus leaving the inner layer 12 covered by the outer layer 14 at the ends of the pipe 10.

A first electrical connector 18 is attached to the exposed inner layer 12 at one end of the pipe 10, and a second electrical connector 19 is attached to the exposed inner layer 12 at the other end of the pipe 10. Both connectors are tightened around the inner layer in a similar manner as a hose clamp is tightened, thus ensuring a good electrical connection between each of the connectors and the inner layer 12.

An electric power source 20 is provided that is operationally connected to the first connector 18 via a first cable 22 and to the second connector 19 via a second cable 24. When installed in an application and with a liquid running through the pipe 10, the electric power source 20 is set to supply a direct current in the inner layer 12 that is between 0.3 mA and 0.7 mA by way of the electric circuit established with the first connector 18, the second connector 19, the first cable 22, and the second cable 24. In an alternative embodiment, the electric power source 20 is also set to generate a stable potential in the range 50 V and 70 V between the first connector 18 and the second connector 19.

In alternative embodiments, the electric power source 20 is set to supply an alternating current in the inner layer 12 that is between 0.4 mA and 0.8 mA. Additionally or alternatively, the electric power source 20 is also set to generate a stable potential in the range 50 V and 70 V between the first connector 18 and the second connector 19.

The electric power source 20 is operated to supply a continuous electric current to the inner layer 12. In an alternative embodiment, the electric current is pulsed or intermittently operated. In one embodiment, the electric current is supplied in a cycle alternating between one week of electric current supply and one week without electric current supply, thus effectively having a combined pulse length over a period of time that is 50% of the length of the period.

Figure 2:
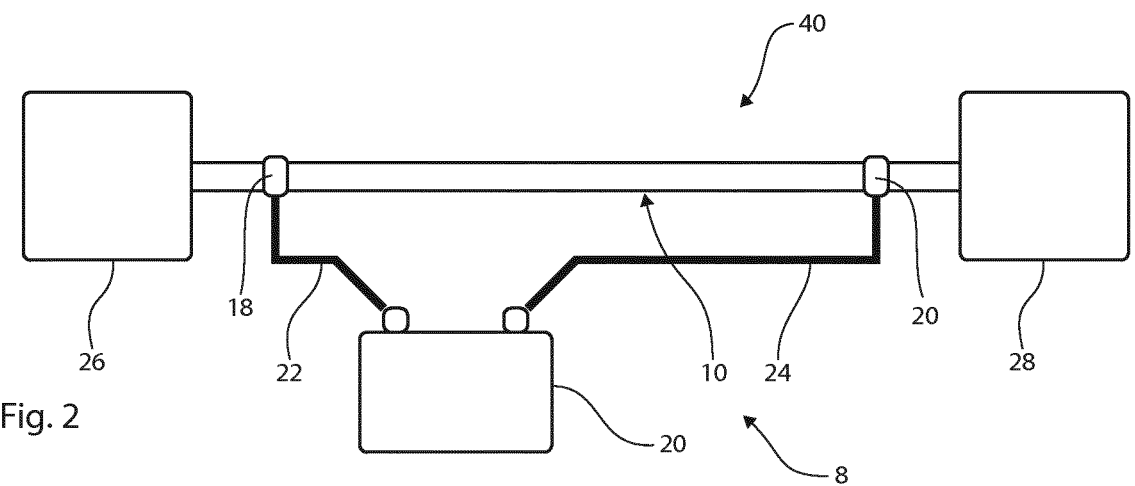

An embodiment of the proposed system 8 is shown in FIG. 2. The system 8 is installed in a liquid transportation application 40. It has all the features of the system 8 described above in relation to FIG. 1. At one end, the pipe 10 is connected to a liquid supply 26, for example public water mains. At the other end, the pipe 10 is connected to a liquid recipient 28, such as the water inlet at a domestic or industrial building, or another section of the public water mains.

Figure 3:
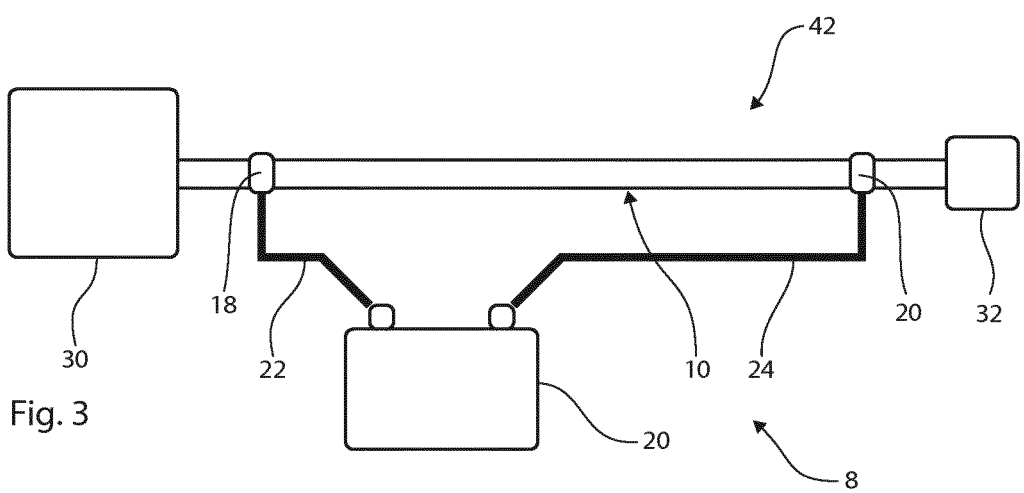

FIG. 3 schematically illustrates an embodiment of the proposed system 8 in a liquid dispensing application. The system 8 has all the features described above in relation to FIG. 1. At one end, the pipe 10 is connected to a liquid supply 30, for example a hot-water pipe in a domestic building. At the other end, the pipe 10 is connected to a liquid dispenser 32, such as a shower in a domestic or public building.

Figure 4:
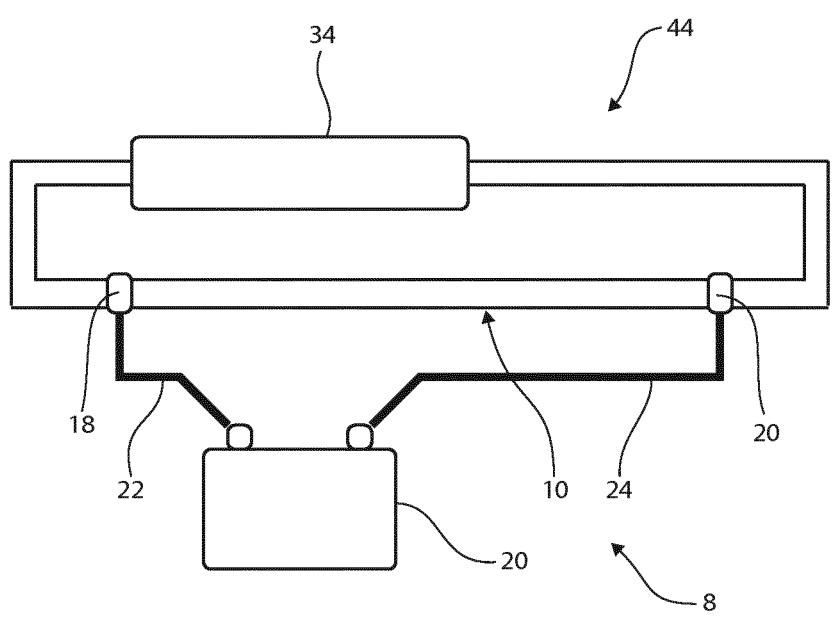

Another embodiment of the proposed system 8 is shown in FIG. 4. The system 8 is installed in a liquid recycling application 44. It has all the features of the system 8 described above in relation to FIG. 1. At both its ends the pipe 10 is connected to liquid recycler 28, such as the heat exchanger, the circulation pump, and the radiators of a low-temperature heating system of a building.

Figure 5:
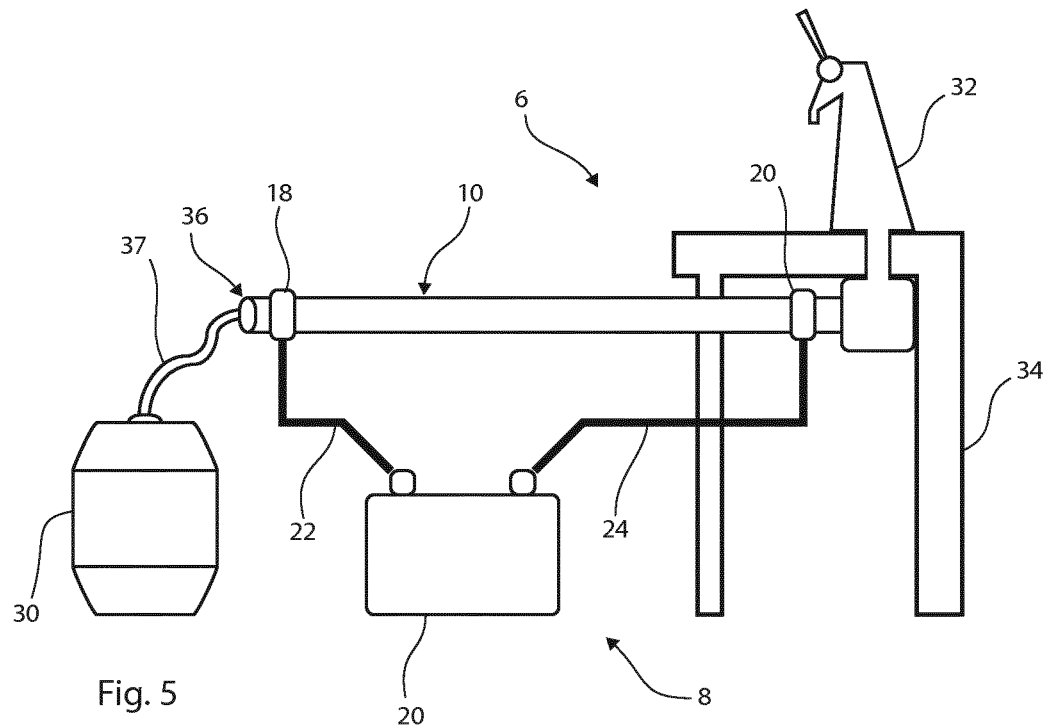

An embodiment of a beverage dispensing system 6 is schematically illustrated in FIG. 5. The dispensing system 6 has a liquid dispenser or tapping station for the beverage in the form of a beer tap 32 attached to a bar counter 34. It further has a beverage conduit 36 for conveying a beverage from a liquid supply or container containing the beverage in the form of a beer keg 30. A system 8 for preventing microbiological growth having the features of the embodiment described above in relation to FIG. 1 forms part of the dispensing system 6. The pipe 10 constitutes a portion of the beverage conduit 6. At one end, the pipe 10 is connected to the beer keg 30 via a beverage hose 37. At its other end, the pipe 10 is connected to the beer tap 32. When the electric power source 20 is operated as described above in relation to FIG. 1, microbiological growth is prevented in the pipe 10.

Figure 6:
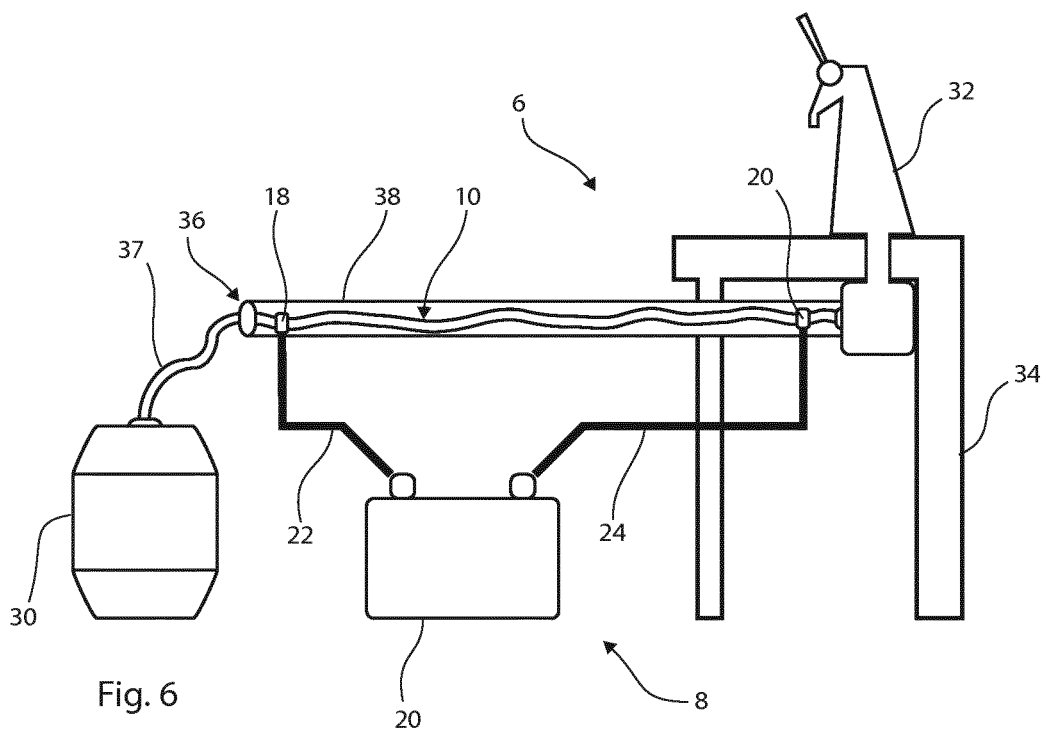

Another embodiment of a beverage dispensing system 6 is schematically illustrated in FIG. 6. The dispensing system 6 has a liquid dispenser or tapping station for the beverage in the form of a beer tap 32 attached to a bar counter 34. A system 8 for preventing microbiological growth, having the features of the embodiment described in relation to FIG. 1, forms part of the dispensing system 6. However, the system 8 differs in that the pipe 10 is a hose. The dispensing system 6 has an existing conduit 38 in the form of a rigid pipe 38. The hose 10 has been retrofitted in the rigid pipe 38 by the insertion of the hose 10 through the receiving end of the rigid pipe 38 and by connecting the hose 10 to the beer tap 32. At one end, the hose 10 is connected to a beer keg 30 via a beverage hose 37. Thus, the hose 10 forms part of a beverage conduit 36 conveying beer from the keg 30 to the beer tap 32. When the electric power source 20 is operated as described above in relation to FIG. 1, microbiological growth is prevented in the hose 10.

Proof-of-Concept

An investigation of the proposed technology has been performed including three different setups. Three pipes of identical length and diameter were used. The length was 25 meter and the inner diameter was 63 mm. In the first setup, the pipe was a single-layer polyethylene pipe. In the second and third setups the pipes were identical multi-layered pipes with an inner layer of carbon-black-filled polyethylene. Electrical connectors were attached to the inner layer of the pipes at the ends of the pipes. Sweet water from public water mains was introduced in and allowed to flow through the pipes. An electric current of 0.5 mA was supplied to the electrical connectors of the third setup at a voltage in the range 60 V to 65 V.

The investigation was divided into two periods, the first period covering weeks 1 to 10 and the second period covering weeks 10 to 25.

Microbiological growth was monitored weekly by the taking of samples of the biofilm from the inner walls of the pipes. The samples were cultivated for 48 hours and the number of bacteria colonies was then calculated in each sample and used to represent the microbiological growth in the corresponding setup.

In the first period, the microbiological growth was allowed to settle on the inner walls and allowed to adjust to the environment inside the pipes. No conclusive results were achieved in the first period. The three setups were then moved and connected to the public mains at another point before the second period of investigation started.

Figure 7:
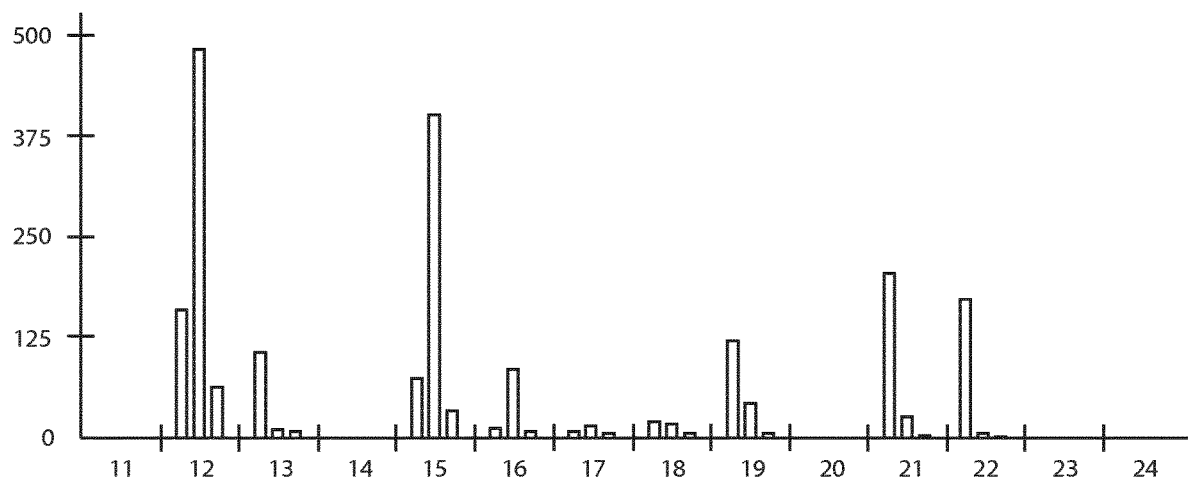
FIG. 7 is a graph illustrating the results of an investigation of the function of the proposed technology.

The results of the second period are shown in FIG. 7. The weeks are indicated on the abscissa and the number of counted bacteria is indicated on the ordinate. For each week, the left bar represents the measurement from the first setup, i.e. with a single layer polyethylene pipe, the middle bar represents the measurement from the second setup, i.e. with an inner conductive layer without an electric current, and the right bar represents the measurement from the third setup, i.e. with an inner conductive layer with an electric current. It should be noted that no sampling was performed in the weeks without any bars.

As can be clearly seen in FIG. 7, after week 16 when the microbiological growth had established itself in the pipes, the microbiological growth in the second setup was greater than in the third setup, thus showing that the supplied electric current reduces the microbiological growth. It is contemplated that the high initial counts of the second and third setups is a result of an initial adaption to the environment inside the pipes with carbon-black in the inner layer.

ITEM LIST 6 beverage dispensing system
8 system
10 pipe or hose
12 inner layer
14 outer layer
16 inside of the pipe
18 first electrical connector
19 second electrical connector
20 electric power source
22 first cable 24 second cable
26 liquid supply
28 liquid recipient
30 liquid supply
32 liquid dispenser
34 bar counter
36 a beverage conduit
37 beverage hose
38 existing conduit
40 liquid transportation application
42 liquid dispensing application
44 liquid recycling application

The invention claimed is:

1. A system for preventing microbiological growth in a conduit conveying a liquid, wherein the system comprises:
    a multi-layered pipe constituting said conduit and having an inner layer and an outer layer, wherein the inner layer is formed of an electrically conductive polymer material and covers an inside surface of the pipe so as to be directly contacted by liquid in the pipe, wherein the inner layer has an outside, a portion of which is covered by the outer layer, and wherein the outer layer is formed of an electrically insulating polymer material;
    a first electrical connector connecting to a first exposed portion of the inner layer from outside the pipe, and a second electrical connector connecting to a second exposed portion of the inner layer from outside the pipe, wherein the first electrical connector and the second electrical connector are electrically connected to each other by the inner layer; and
    an electric power source operationally connected to the first electrical connector and the second electrical connector, the electric power source being configured for supplying an electric current to the inner layer.

2. The system according to claim 1, wherein the electric current is a direct current.

3. The system according to claim 2, wherein the electric current is between 0.1 mA and 10 mA.

4. The system according to claim 1, wherein the electric current is supplied at a voltage between the first electrical connector and the second electrical connector that is between 20 V and 150 V.

5. The system according to claim 1, wherein the electric current is an alternating current.

6. The system according to claim 5, wherein the electric current is between 0.1 mA and 10 mA.

7. The system according to claim 5, wherein the electric current is supplied at a voltage between the first electrical connector and the second electrical connector that is between 20 V and 80 V.

8. The system according to claim 5, wherein the alternating current has a frequency between 1 kHz and 5 kHz.

9. The system according to claim 1, wherein the power source is further configured for supplying a pulsed electric current.

10. The system according to claim 9, wherein the pulses have a combined pulse length over a period of time that is equal to or less than 50% of the length of the period.

11. The system according to claim 1, wherein the electrically conductive polymer material of the inner layer is carbon-black filled polyethylene.

12. The system according to claim 1, wherein the multi-layered pipe is a flexible hose.

13. The system according to claim 12, wherein the electrically conductive polymer material of the inner layer is carbon-black filled polyethylene.

* * * * *